United States Patent [19]

Hansen

[11] Patent Number: 5,776,131
[45] Date of Patent: Jul. 7, 1998

[54] DEVICE FOR CAUTERIZING HORN BUTTONS AND HORN STUMPS IN CATTLE

[76] Inventor: Donald C. Hansen, 305 Center St., Shelby, Iowa 51570

[21] Appl. No.: 614,985

[22] Filed: Mar. 12, 1996

[51] Int. Cl.⁶ ............................................. A61B 17/36
[52] U.S. Cl. ............................ 606/49; 126/403; 126/406; 606/163
[58] Field of Search .................. 606/49, 116, 163, 606/174, 170; 126/403, 406, 413, 414, 402, 404–407; 30/228, 181

[56] References Cited

U.S. PATENT DOCUMENTS

| | | |
|---|---|---|
| 724,002 | 3/1903 | Freytag. |
| 2,582,450 | 1/1952 | Mims ................................ 128/303.1 |
| 3,676,929 | 7/1972 | Nicholson ........................ 30/228 X |
| 3,828,431 | 8/1974 | Fleming et al. .................. 30/228 X |
| 3,828,789 | 8/1974 | Young .............................. 128/303.1 |
| 4,345,377 | 8/1982 | Hewes, Jr. ........................ 30/181 |
| 4,474,178 | 10/1984 | Hyatt ............................. 606/163 |
| 4,920,951 | 5/1990 | Le Marchand et al. ......... 126/403 X |

Primary Examiner—Robert L. Nasser
Assistant Examiner—Ryan Carter
Attorney, Agent, or Firm—Henderson & Sturm

[57] ABSTRACT

A flammable gas heated cauterizing device for use in cauterizing the horn stumps in older cattle as well as removing the horn buttons from young calves. A propane torch having a burner tube is utilized to heat a cauterizing device fabricated from surgical stainless steel. A first embodiment, for cauterizing larger horn stumps, comprises a torch attachment tube spot welded to a cauterizing tip having a flat cauterizing face with rearwardly extending frustoconical tubular sidewalls. A second embodiment, for cauterizing horn buttons, is identical to the first embodiment but utilizes a concave cauterizing tip. The invention heats up much faster and to a much higher temperature than the prior art devices, thereby making the cauterizing process much quicker and less painful for the animals.

4 Claims, 2 Drawing Sheets

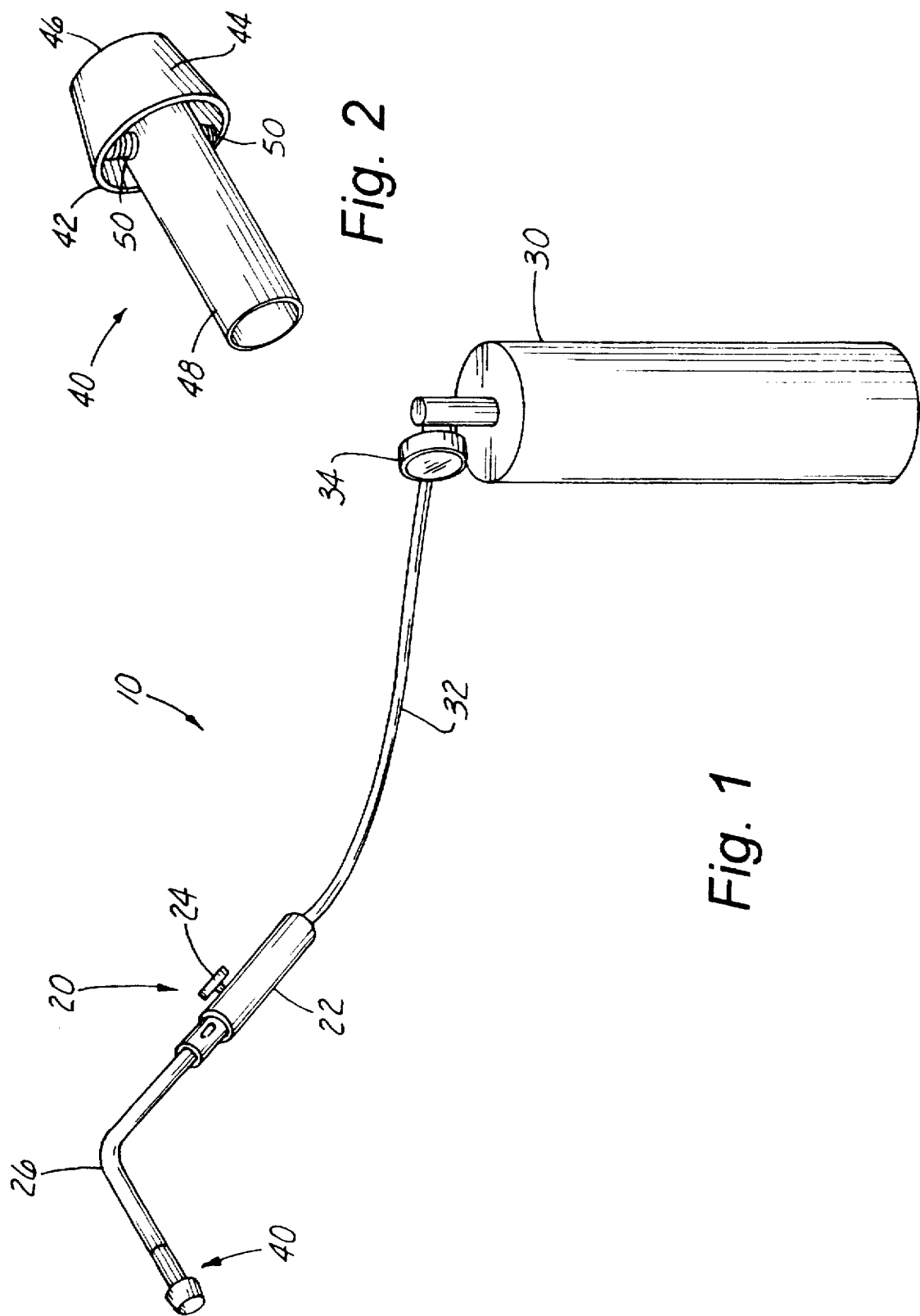

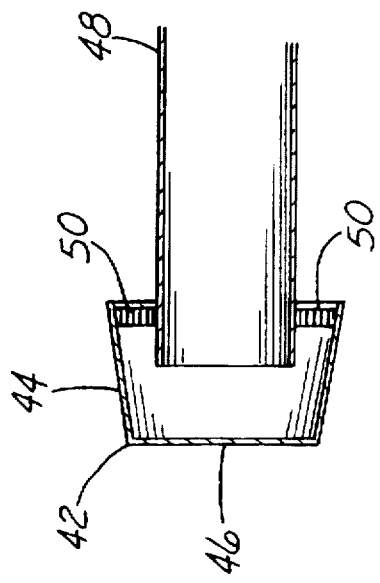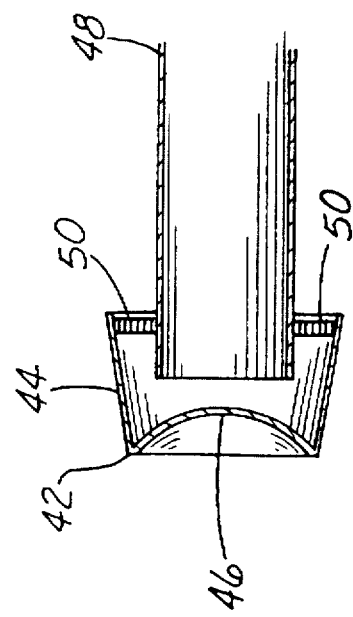

5,776,131

DEVICE FOR CAUTERIZING HORN BUTTONS AND HORN STUMPS IN CATTLE

TECHNICAL FIELD

The present invention relates generally to dehorning equipment for cattle, and more particularly to a device for cauterizing horn buds in young calves and horn stumps in older cattle.

BACKGROUND ART

When dehorning young calves, current procedures include (1) cauterizing the horn button with sufficient heat to destroy the horn cells; (2) cutting the horn button out and then cauterizing the wound, or (3) applying an acid to the horn button to destroy the horn cells. Dehorning older cattle requires cutting the horn off near its base and then cauterizing the wound to stop bleeding and destroy nerve cells.

The most common cauterizing device is the branding iron type in which a cylindrical block of steel having a concave face is heated in a branding pot and then applied over the calve's horn button. Electric dehorners are also available which heat a concave steel surface to a sufficient temperature to destroy the horn cells of the horn button. There is also a gas powered horn button cauterizer with an internal burner utilized to heat a small concave steel surface. While these devices are often adequate for the limited purpose of removing horn buttons from young calves, they are not designed to cauterize the larger horn stumps in older cattle.

DISCLOSURE OF THE INVENTION

The present invention discloses a flammable gas heated cauterizing device for use in cauterizing the horn stumps in older cattle as well as removing the horn buttons from young calves. A propane torch having a burner tube is utilized to heat a cauterizing device fabricated from surgical stainless steel. A first embodiment, for cauterizing larger horn stumps, comprises a torch attachment tube spot welded to a cauterizing tip having a flat cauterizing face with rearwardly extending frustoconical tubular sidewalls. A second embodiment, for cauterizing horn buttons, is identical to the first embodiment but utilizes a concave cauterizing tip. The invention heats up much faster and to a much higher temperature than the prior art devices, thereby making the cauterizing process much quicker and less painful for the animals.

BRIEF DESCRIPTION OF THE DRAWINGS

These and other attributes of the invention will become more clear upon a thorough study of the following description of the best mode for carrying out the invention, particularly when reviewed in conjunction with the drawings, wherein:

FIG. 1 is a respective view of flammable gas torch utilizing the cauterizing device of the present invention;

FIG. 2 is a perspective view of the invention;

FIG. 3 is a side sectional view of a first embodiment of the cauterizing device; and FIG. 4 is a side sectional view of a second embodiment of the cauterizing device.

BEST MODE FOR CARRYING OUT THE INVENTION

Referring now to the drawings, wherein like reference numerals designate identical or corresponding parts throughout the several views, the flammable gas torch utilizing the cauterizing device of the present invention is depicted at 10 in FIG. 1 and comprises a propane torch 20 with a handle 22 with a gas adjustment valve 24 from which extends a burner tube 26, as is well known in the art. The torch 20 is connected to a propane tank 30 by means of a gas supply tube 32 and a regulator 34, also well known in the art. The cauterizing device of the present invention 40 slides over the end of the burner tube 26 and is held thereon by friction.

Referring now to FIGS. 2, and 3, a first embodiment of the cauterizing device 40, preferably fabricated from surgical stainless steel, is seen to comprise a cauterizing tip 42 having a frustoconical, tubular sidewall 44 and a flat cauterizing surface 46. A torch attachment tube 48 is spot welded 50 within the tubular sidewall 44 in a spaced apart relationship with the cauterizing surface 46 and the tubular sidewall 44. Flame from the torch 20 passes from the burner tube 26 through the attachment tube 48 to within the cauterizing tip 42, and is then directed rearwardly through the annular passageway between the attachment tube 48 and the tubular sidewall 44. This arrangement allows flame from the torch to impinge directly on the cauterizing surface 46 for maximum heating, but then directs and disperses the flame rearwardly, away from the cattle's head and ears. This first embodiment is particularly designed for cauterizing the horn stumps of larger cattle.

A second embodiment of the cauterizing device is depicted in FIG. 4 which is useful for cauterizing the horn buttons of young calves. In this embodiment, the cauterizing surface 46 is concave rather than flat and may therefore be placed directly over the horn button.

Those skilled in the art will recognize that many modifications and variations of the present invention are possible in light of the above teachings. It is therefore to be understood that, within the scope of the appended claims, the invention may be practiced otherwise than as specifically described.

What is claimed is:

1. A device for cauterizing horn buttons and horn stumps in cattle comprising:

(a) cauterizing tip having a cauterizing surface formed integrally with a rearwardly projecting frustoconical tubular sidewall;

(b) a flammable gas torch including a torch attachment tube secured on a first end to a burner tube of the flammable gas torch, wherein a second end of the torch attachment tube is suspended within said cauterizing tip at a location spaced from both said cauterizing surface and said frustoconical tubular sidewall; and, (c) securing means for suspending said second end of said torch attachment tube within said cauterizing tip.

2. The device as in claim 1 wherein said securing means comprises:

a pair of spot welds disposed on opposite sides of said second end of the attachment tube and said cauterizing tip for suspending said second end of said torch attachment tube within said cauterizing tip.

3. The device as in claim 1, wherein, said cauterizing surface is flat.

4. The device as in claim 1, wherein said cauterizing surface is concave.

* * * * *